United States Patent
Waldmann

(10) Patent No.: US 9,179,226 B2
(45) Date of Patent: Nov. 3, 2015

(54) PARTIALLY IMPLANTABLE HEARING DEVICE

(75) Inventor: Bernd Waldmann, Maur (CH)

(73) Assignee: Advanced Bionics AG (CH)

(*) Notice: Subject to any disclaimer, the term of this patent is extended or adjusted under 35 U.S.C. 154(b) by 542 days.

(21) Appl. No.: 12/864,380

(22) PCT Filed: Feb. 7, 2008

(86) PCT No.: PCT/EP2008/000959
§ 371 (c)(1),
(2), (4) Date: Aug. 27, 2010

(87) PCT Pub. No.: WO2008/049933
PCT Pub. Date: May 2, 2008

(65) Prior Publication Data
US 2011/0015466 A1 Jan. 20, 2011

(51) Int. Cl.
*H04R 25/00* (2006.01)
*A61N 1/36* (2006.01)

(52) U.S. Cl.
CPC ............ *H04R 25/554* (2013.01); *H04R 25/606* (2013.01); *A61N 1/36032* (2013.01)

(58) Field of Classification Search
CPC ............ H04R 25/606; H04R 2225/67; A61N 1/36032
USPC ............ 600/25; 181/129; 381/312–331, 23.1; 607/55–57
See application file for complete search history.

(56) References Cited

U.S. PATENT DOCUMENTS

| 4,606,329 | A | * | 8/1986 | Hough ............................. 600/25 |
| 4,776,322 | A | | 10/1988 | Hough et al. |
| 5,277,694 | A | | 1/1994 | Leysieffer et al. |
| 5,906,635 | A | * | 5/1999 | Maniglia .......................... 607/57 |
| 6,005,955 | A | * | 12/1999 | Kroll et al. ...................... 381/328 |
| 6,123,660 | A | * | 9/2000 | Leysieffer ........................ 600/25 |
| 6,137,889 | A | * | 10/2000 | Shennib et al. ............... 381/328 |
| 6,162,169 | A | | 12/2000 | Leysieffer |
| 6,620,094 | B2 | | 9/2003 | Miller |
| 6,697,674 | B2 | * | 2/2004 | Leysieffer ....................... 607/57 |

(Continued)

FOREIGN PATENT DOCUMENTS

| WO | 9501710 | | 1/1995 | |
| WO | WO 9501710 A1 | * | 1/1995 | ............. H04R 25/00 |
| WO | 9906108 | | 2/1999 | |
| WO | WO 9906108 A1 | * | 2/1999 | ............. A61N 1/378 |

OTHER PUBLICATIONS

International Search Report, International Application No. PCT/EP2008/000959, Dated Apr. 22, 2008.

Primary Examiner — John Lacyk
(74) Attorney, Agent, or Firm — Conley Rose, P.C.

(57) ABSTRACT

A partially implantable hearing device comprises a microphone assembly to be worn by the user for capturing audio signals from ambient sound, an audio signal processing unit for processing the audio signals captured by the microphone and an implantable assembly with a power supply and an electromechanical output transducer for stimulating the user's hearing according to the audio signals processed by the audio signal processing unit. Also a microphone assembly provides for transcutaneous transmission of audio signals captured by the microphone assembly to the implantable assembly and for transcutaneous transmission of power to microphone assembly from the implantable assembly.

13 Claims, 2 Drawing Sheets

(56) References Cited

U.S. PATENT DOCUMENTS

| | | | |
|---|---|---|---|
| 7,251,530 B1* | 7/2007 | Overstreet et al. | 607/55 |
| 2004/0172102 A1* | 9/2004 | Leysieffer | 607/57 |
| 2004/0247146 A1* | 12/2004 | Killion et al. | 381/312 |
| 2005/0226447 A1 | 10/2005 | Miller | |
| 2005/0251225 A1* | 11/2005 | Faltys et al. | 607/57 |
| 2005/0267549 A1 | 12/2005 | Santina et al. | |
| 2006/0183965 A1* | 8/2006 | Kasic et al. | 600/25 |
| 2007/0100395 A1* | 5/2007 | Ibrahim | 607/60 |

\* cited by examiner

PARTIALLY IMPLANTABLE HEARING DEVICE

CROSS-REFERENCE TO RELATED APPLICATIONS

This application is a national phase entry of prior PCT Application No. PCT/EP2008/000959 filed Feb. 7, 2008 and entitled "Partially Implantable Hearing Device", the disclosure of which is herein incorporated by reference.

BACKGROUND OF THE INVENTION

1. Field of the Invention

The invention relates to a partially implantable hearing device comprising an electro-mechanical output transducer.

2. Description of Related Art

Implantable hearing devices are a class of medical devices for treatment of sensor neural and/or conductive hearing loss of patients who are unable or unwilling to use a conventional hearing aid. The main components of an implantable hearing device are a microphone, an audio signal processing unit, an output transducer for stimulating the user's hearing and a power supply, i.e. a battery. In general, the output transducer may be an electro-mechanical transducer which is used for stimulating a member of the ossicular chain or for directly stimulating the inner ear or which is part of a bone-anchored hearing aid (BAHA), or an electrical stimulator for a cochlear implant, or a combination thereof. If all of these components are implanted, the implantable hearing device is categorized as a fully implantable device. If at least one component remains outside the body, the device is categorized as a partially implantable hearing device; in this case, it requires additional components to transfer power and information between the implanted part and the external part.

Fully implantable devices are beneficial in that they are completely invisible and do not restrict daily activities such as swimming or vigorous movement. However, such devices have to deal with considerable technical challenges related to the implantable microphone which must be biologically stable, which should have low sensitivity to body-generated vibrations such as chewing sounds, and which should not cause feedback squealing by picking-up the output vibration or electrical by-products of the function of the amplifier and transducer. Current fully implantable devices are limited in their available gain, typically due to feedback problems related to either the vibration sensitivity of a microphone covered by a massive layer of skin or to the proximity between the microphone and the output transducer.

A typical design of partially implantable devices has all components except the output transducer outside the body. While this design avoids the microphone challenges of fully implantable devices, it requires large and heavy outside components which are typically held in place by implanted magnets to ensure proper alignment of the implanted and external parts of the transcutaneous link used to transmit power and information into the implanted part of the device. Thus, current partially implantable devices contain bulky, conspicuous external parts, which house the power supply and the audio signal processing electronics, and they are not water-proof, because they contain openings in the housing for access to replaceable batteries, etc. Typically the largest share of the overall power consumption is due to the output transducer. Transcutaneous power transmission is not very efficient, due to technical and physical constraints. Therefore, in conventional partially implantable devices wherein the power source is located outside the body overall power consumption is relatively high, because a significant amount of power is lost in the transcutaneous link, whereby the required size of the power source is increased or the lifetime of the rechargeable or replaceable external battery is reduced.

U.S. Pat. No. 6,620,094 B2 describes a fully implantable hearing device and, as an alternative, a conventional partially implantable hearing device wherein only the electro-mechanical output transducer is implanted, while the external portion comprises the microphone, the audio signal processing electronics and the power source. A further example of a fully implantable hearing device comprising an electro-mechanical transducer is described in U.S. Pat. No. 5,277,694. Also U.S. Pat. No. 6,162,169 relates to a partially or fully implantable hearing device comprising an electro-mechanical output transducer. A further example of a conventional partially implantable hearing device is described in US 2005/0226447 A1.

US 2005/0267549 A1 relates to a cochlear implant device which, according to one embodiment, is a fully implantable device and which, according to an alternative embodiment, is a partially implantable device wherein the implantable part includes the cochlear stimulator, the signal processing electronics and the power source, whereas the external part includes a completely-in-the-canal (CIC)-microphone which is connected to the implantable part via a transcutaneous link.

It is an object of the invention to provide for an implantable hearing device comprising an electro-mechanical output transducer, which device allows for relatively high gain and for comfortable use by the patient.

SUMMARY OF THE INVENTION

According to the invention this object is achieved by a partially implantable hearing device as defined in claim 1.

The invention is beneficial in that, by locating the power supply together with the electro-mechanical output transducer in an implantable assembly, while locating the microphone in an external microphone assembly which is supplied with power from the implantable assembly via a transcutaneous wireless link, the feedback problems encountered with the implanted microphone of a fully implanted hearing device are avoided, while nevertheless the volume of the external assembly can be kept relatively small due to the fact that the external assembly is powered by the implanted power supply and hence does not need to include any power supply.

Further, since the microphone assembly does not require openings in the housing for access to a battery etc., the microphone assembly may have a robust and waterproof design. While the transcutaneous link may be inefficient, the absolute amount of power loss is relatively small. Since the microphone—unlike in fully implantable devices—is arranged in an external microphone assembly and hence is not covered by a skin flap, it is possible to design the microphone to have low vibration sensitivity in order not to pick-up body vibrations.

According to one embodiment, the audio signal processing unit necessary for processing the captured audio signals is included in the implantable assembly. In this case the microphone assembly requires only the microphone to be included which can be powered easily through the transcutaneous link from the implanted power supply due to the relatively low power consumption of the microphone compared to that of the output transducer. This embodiment provides for a particularly efficient power unitization, since the losses involved in the transcutaneous link are minimized.

According to another embodiment, the audio signal processing unit included in the microphone assembly rather than in the implantable assembly. This design makes it particularly easy to upgrade the signal processing when new technology becomes available, because no surgical intervention is needed to replace the signal processor.

Further preferred embodiments of the invention are mentioned in the dependent claims.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
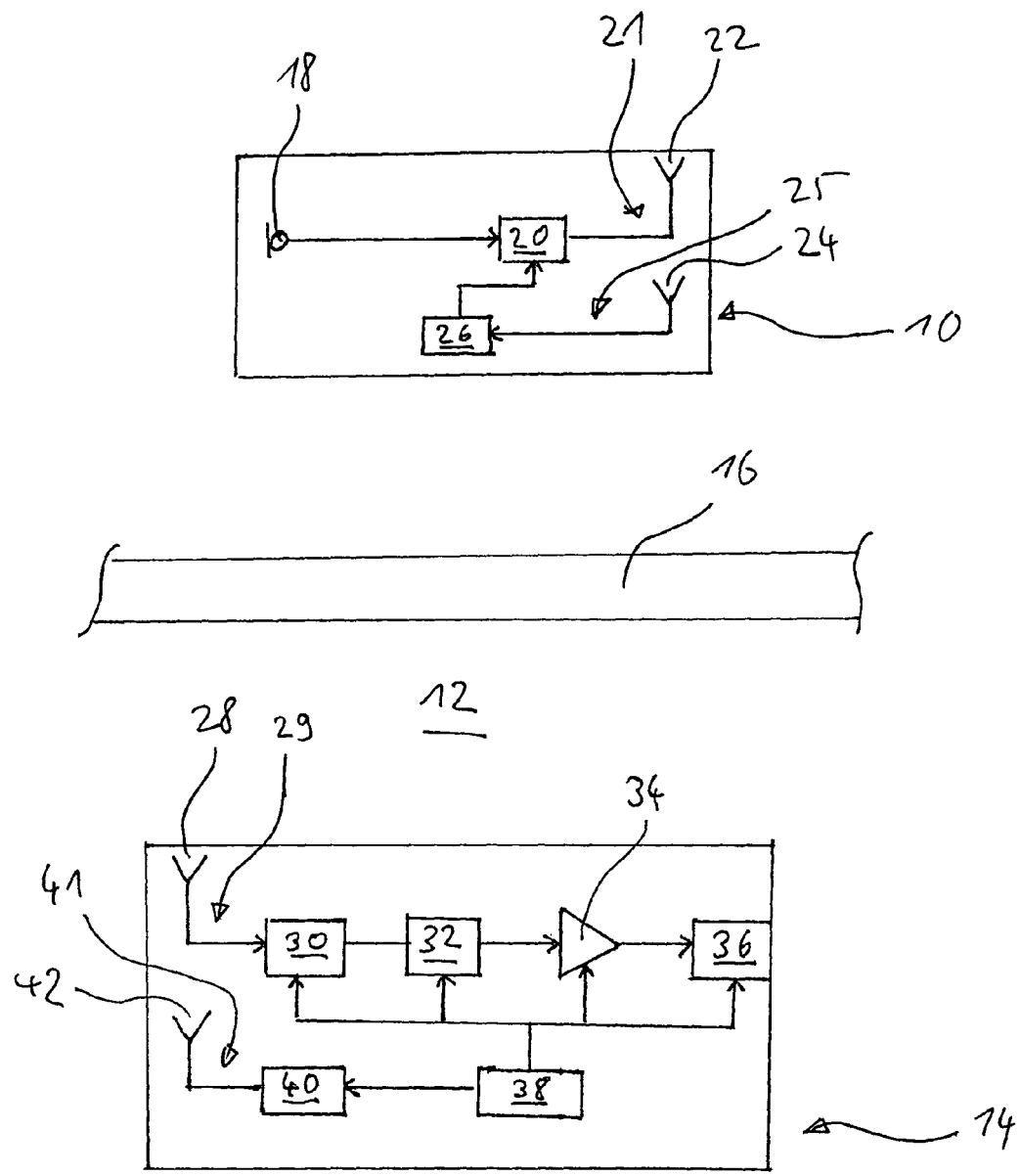
FIG. 1 is a schematic diagram of a first embodiment of the invention.

FIG. 1 shows a partially implantable hearing device comprising a microphone assembly 10 which is worn outside the user's body 12 and an implantable assembly 14 which is implanted under the skin 16. According to one embodiment, the microphone assembly 10 is placed over the user's mastoid bone, and the fully implantable assembly 14 is embedded in the mastoid bone underneath. According to an alternative arrangement, the microphone assembly 10 is placed in the user's ear canal, and the implantable assembly 14 is placed in the mastoid behind the ear canal.

Preferably, the microphone assembly 10 is attachable to the user's skin 16 by a bio-compatible glue such as one used for adhesive bandages. The microphone assembly 10 may be designed to be water-proof or at least splash-proof by using, for example, technologies known from conventional hearing aids or mobile telephones. Preferably, the microphone assembly is relatively flat, having a thickness of less than 3 mm.

The microphone assembly 10 comprises at least one microphone 18 (in order to enable acoustic beam-forming, a plurality of spaced-apart microphones may be provided) for capturing audio signals from ambient sound and signal transmission circuitry 21 comprising a transmission unit 20 connected to a transmission antenna 22, in order to enable transcutaneous transmission of audio signals captured by the microphone 18. The microphone assembly 10 also comprises circuitry 25 for receiving power from the implantable assembly 14, including a power-receiving antenna 24 and a power-receiving unit 26, which supplies the received power to the transmission unit 20, in order to power the microphone 18 and the transmission circuitry 21. The power-receiving antenna 24 may be designed as a coil surrounding an acoustic membrane of the microphone 18, in order to provide for a compact and flat design of the microphone assembly 10.

The implantable assembly 14 comprises signal receiving circuitry 29 comprising a receiving antenna 28 and a receiver unit 30 for receiving the audio signals sent by the microphone assembly 10 via the transcutaneous link, an audio signal processing unit 32 followed by a power amplifier 34, and an electro-mechanical output transducer 36 for stimulating the user's hearing according to the audio signals processed and amplified by the audio signal processing unit 32. The audio signal processing unit 32 may be used for analyzing, shaping and modifying the audio signal in a manner known from conventional hearing aids in order to adjust the audio signal for the user's communication needs and listening preferences. The implantable assembly 14 also comprises a power supply (battery) 38 and power transmission circuitry 41 comprising a power transmission unit 40 and a power transmission antenna 42 for transmitting power to the microphone assembly 10 via a transcutaneous link. The power supply 38 also serves to power the receiver unit 30, the audio signal processing unit 32, the power amplifier 34 and the output transducer 36. The output transducer 36 may be coupled to a member of the ossicular chain, directly to the inner ear, to the skull like in BAHA-systems, or to the cerebrospinal fluid, as it is known in the art.

In the embodiment of FIG. 1, the microphone assembly 10 is adapted to transmit the audio signals as captured by the microphone 18, i.e. without shaping or modifying of the audio signals, to the implantable assembly 14. This design minimizes the power which has to be transmitted through the transcutaneous link.

Figure 2:
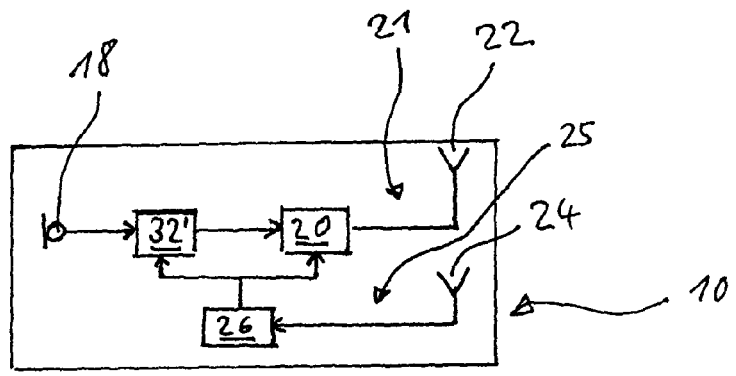
FIG. 2 is a schematic diagram of an alternative embodiment of the invention.
Figure 2:
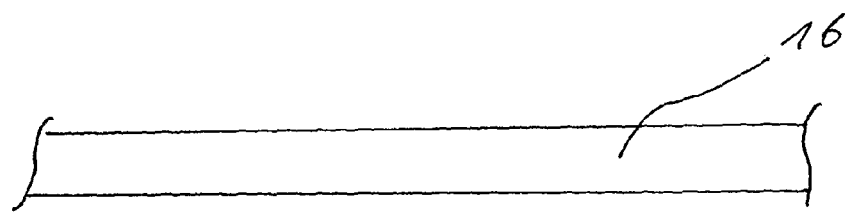
Figure 2:
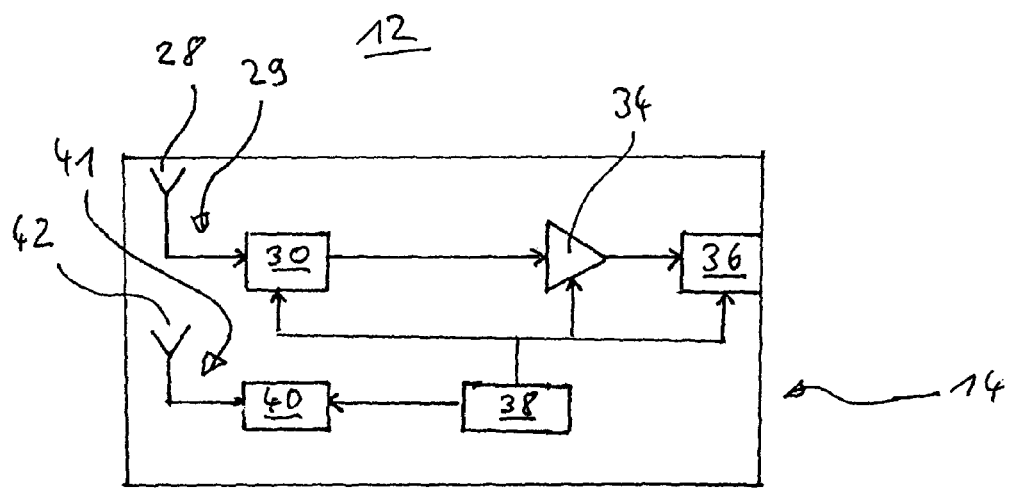

In FIG. 2 a modified embodiment of the invention is shown wherein an audio signal processing unit 32' is provided as part of the microphone assembly 10 rather than as part of the implantable assembly 14. The audio signal processing unit 32' serves to process the audio signals captured by the microphone 18 prior to transmitting the audio signals via the transmission unit 20 and the antenna 22 to the implantable assembly 14 and thereby performs the function of the audio signal processing unit 32 of the embodiment of FIG. 1. According to the embodiment of FIG. 2, the audio signal processing unit 32 has been removed from the implantable assembly 14. The design according to FIG. 2 makes it particularly easy to upgrade the signal processing when new technology becomes available, because no surgical intervention is needed to replace the signal processor.

In all embodiments, the implantable assembly 14 may contain logic that assesses the link quality with the microphone assembly 10 and creates audible signals that guide the user of the system in aligning the microphone assembly 10, in particular the transmit and receive coils thereof, with the implantable assembly 14, in particular the transmit and receive coils thereof.

The present invention provides for a partially implantable hearing device which is functionally equivalent to a fully implantable device in that it may be water-proof and compatible with vigorous movement, without encountering the typical problems of fully implantable devices, such as microphone bio-compatibility and microphone vibration sensitivity.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

The invention claimed is:

1. A partially implantable hearing device for a user, comprising
    a microphone assembly to be worn by the user outside a user's body and comprising at least one microphone for capturing audio signals from ambient sound;
    an audio signal processing unit for processing the audio signals captured by the microphone; and
    an implantable assembly comprising a power supply and an electromechanical output transducer for stimulating the user's hearing according to the audio signals processed by the audio signal processing unit,
    the microphone assembly comprising means for transcutaneous transmission of audio signals captured by the microphone assembly to the implantable assembly and means for receiving power; and the implantable assembly comprising means for receiving the audio signals transmitted from the microphone assembly and means for powering the microphone assembly by transcutaneous transmission of power to the microphone assembly.

2. The hearing device of claim 1, wherein the microphone assembly is attachable to the user's skin by a bio-compatible adhesive.

3. The hearing device of claim 1, wherein the means for receiving power comprises an antenna configured as a coil surrounding an acoustic membrane of the microphone.

4. The hearing device of claim 1, wherein the microphone assembly is configured to be waterproof or splash-proof.

5. The hearing device of claim 1, wherein the microphone assembly comprises the audio signal processing unit in order to process the audio signals captured by the microphone prior to transmitting the audio signals to the implantable assembly.

6. The hearing device of claim 1, wherein the implantable assembly comprises the audio signal processing unit and wherein the microphone assembly is adapted to transmit the audio signals as captured by the microphone to the implantable assembly.

7. The hearing device of claim 1, wherein the microphone assembly has a thickness of less than 3 mm.

8. The hearing device of claim 1, wherein the microphone assembly is configured to be placed over the user's mastoid bone and the implantable assembly is designed to be embedded in the mastoid bone underneath.

9. The hearing device of claim 1, wherein the microphone assembly is configured to be placed in the user's ear canal and the implantable assembly is designed to be placed in a mastoid behind the ear canal.

10. The hearing device of claim 1, wherein the electromechanical transducer is configured to be coupled to a member of an ossicular chain, directly to an inner ear, to a skull or to a cerebrospinal fluid of the user.

11. The hearing device of claim 1, wherein the microphone assembly is configured to be placed over the user's mastoid bone and the implantable assembly is configured to be embedded in the mastoid bone underneath.

12. The hearing device of claim 1, wherein the microphone assembly is configured to be placed in the user's ear canal and the implantable assembly is configured to be placed in a mastoid behind the ear canal.

13. The hearing device of claim 1, wherein the electromechanical transducer is coupled to a member of an ossicular chain, directly to an inner ear, to a skull or to a cerebrospinal fluid of the user.

* * * * *